United States Patent
Brunacci et al.

(10) Patent No.: US 6,341,531 B1
(45) Date of Patent: Jan. 29, 2002

(54) METHOD FOR IMPROVING THE ARCHIVING OF DYNAMIC PARAMETERS

(75) Inventors: Antonio Brunacci, Carisle (GB); Marco Nahmias Nanni, Milan; Antonio Serra, Genoa, both of (IT)

(73) Assignee: Pirelli Pneumatici S.p.A., Milan (IT)

( * ) Notice: Subject to any disclaimer, the term of this patent is extended or adjusted under 35 U.S.C. 154(b) by 0 days.

(21) Appl. No.: 09/428,493

(22) Filed: Oct. 28, 1999

Related U.S. Application Data

(60) Provisional application No. 60/106,081, filed on Oct. 29, 1998.

(30) Foreign Application Priority Data

Oct. 29, 1998 (EP) .............................................. 98203653

(51) Int. Cl.$^7$ ................................................. G01N 3/24
(52) U.S. Cl. ...................................................... 73/841
(58) Field of Search .......................... 73/846, 826, 657, 73/59, 60, 841

(56) References Cited

U.S. PATENT DOCUMENTS

| | | |
|---|---|---|
| 4,299,120 A | 11/1981 | Barker |
| 4,567,774 A | 2/1986 | Manahan et al. |
| 5,079,956 A | * 1/1992 | Burhin et al. .................. 73/846 |
| 5,156,053 A | 10/1992 | Shiraishi et al. |
| 5,253,513 A | 10/1993 | Van Arsdale et al. |
| 5,798,456 A | 8/1998 | Tranquilla |

FOREIGN PATENT DOCUMENTS

| | | |
|---|---|---|
| EP | 0 457 412 | 11/1991 |
| EP | 0 466 060 | 1/1992 |
| EP | 0 867 708 | 9/1998 |

* cited by examiner

*Primary Examiner*—Benjamin R. Fuller
*Assistant Examiner*—Octavia Davis
(74) *Attorney, Agent, or Firm*—Finnegan, Henderson, Farabow, Garrett & Dunner, L.L.P.

(57) ABSTRACT

A method for improving the archiving of a curve plotted from at least N (N≧5) measured experimental values of a dynamic parameter P of a viscoelastic material where this parameter is a function of the deformation q at a given temperature, characterized in that it comprises the following stages:

a) the acquisition of N experimental measurements of the said dynamic parameter P of the said viscoelastic material where this parameter is a function of the deformation q at a predetermined temperature;

b) the determination, by successive approximations, of the values $P_0$, $P_1$, $q_1$, $P_2$, $q_2$, which, when inserted in the relation $$P(q) = P_0 + P_1 e^{-\frac{q}{q_1}} + P_2 e^{-\frac{q}{q_2}} \quad (A)$$

generate the curve which best approximates the experimental curve passing through all the points which represent the N values determined experimentally during the preceding stage a);

c) the archiving of the values $P_0$, $P_1$, $q_1$, $P_2$, $q_2$ found in this way.

8 Claims, 1 Drawing Sheet ic parameter and the value of the deformation corresponding to this measurement) to only 5.

METHOD FOR IMPROVING THE ARCHIVING OF DYNAMIC PARAMETERS

This application is based on European Patent Application No. 98203653.5 filed on Oct. 29, 1998 and U.S. Provisional Application No. 60/106,081 filed on Oct. 29, 1998, the content of which is incorporated hereinto by reference.

BACKGROUND OF THE INVENTION

The present invention relates to a method for improving the archiving of a curve plotted from N measured experimental values of a dynamic parameter of a viscoelastic material where this parameter is a function of the deformation.

Among the properties of viscoelastic materials, those most closely related to their use are the dynamic properties, in other words the responses to the application of deformations.

In order to be able to select, at the moment of use, the material which best meets the final dynamic requirements of a desired product, it is necessary to know the dynamic properties of a large number of materials, and consequently to have made numerous experimental measurements beforehand for the purpose of characterizing them.

For example, in order to determine the dynamic properties of such materials, experimental measurements of the strain are generally made after cycles of deformation. These dynamic properties, however, depend on the temperature and frequency of their measurement. Moreover, for some materials, such as polymers filled with reinforcing materials, or asphalts, the situation is even more complex, since the properties also depend on the applied deformation. Consequently, the characterization of each material requires the acquisition of a large number of experimental values for a variety of temperature, frequency of use and applied deformation, and, subsequently, the archiving of the values thus obtained or of the graphs showing the curves passing through these experimental values. This storage requires long periods of time and paper or data-processing archives which are very large and easily damaged.

The inventors of the present invention, therefore, tackled the problem of simplifying the process of archiving the acquired experimental values of a dynamic parameter of a viscoelastic material where this parameter is a function of the deformation.

More precisely, in the case of the experimental curve, at a given temperature, of any dynamic parameter P as a function of any deformation q applied to a generic test specimen of a viscoelastic material, the inventors of the present invention unexpectedly discovered that this experimental curve could be reduced to a summation of exponentials of the type $$P(q) = P_0 + \sum_{i=1}^{\infty} P_i e^{-\frac{q}{q_i}}$$

where

P(q) is the value of the dynamic parameter as a function of the deformation q;

$P_0$ is the value of the dynamic parameter at infinite deformation;

q is the deformation in question;

$P_i$ is the value of the characteristic dynamic parameter of the i-th deformation;

$q_i$ is the characteristic deformation at which the i-th exponential intervenes.

The inventors also realized that 5 values, namely $P_0$, $P_1$, $q_1$, $P_2$, $q_2$, were sufficient to provide a good approximation of the said experimental curve.

For example, in the case of the experimental curve of the modulus of elasticity G' as a function, at a given temperature, of a torsion γ applied to a cylindrical test specimen consisting of a mix, filled with lampblack, for a tire tread, the inventors found that this experimental curve could be reduced, according to the present invention, to the relation $$G'(\gamma) = G'_0 + G'_1 e^{-\frac{\gamma}{\gamma_1}} + G'_2 e^{-\frac{\gamma}{\gamma_2}}$$

Finally, when they also investigated the experimental curves of the complex modulus G*, of the viscous modulus G" (where $|G^*|=\sqrt{(G')^2+(G'')^2}$), and of the loss factor tanδ (where tanδ=G"/G') as a function of the torsion γ applied to the test specimen, the inventors unexpectedly discovered that these could also be represented by the aforesaid summation of exponentials, and that five corresponding values, as shown above, were sufficient to provide a good approximation to each of the aforesaid experimental curves.

SUMMARY OF THE INVENTION

A first aspect of the present invention is therefore a method for improving the archiving of a curve plotted from at least N (N≧5) measured experimental values of a dynamic parameter P of a viscoelastic material where this parameter is a function of the deformation q at a given temperature, characterized in that it comprises the following stages:

a) the acquisition of N experimental measurements of the said dynamic parameter P of the said viscoelastic material where this parameter is a function of the deformation q at a predetermined temperature;

b) the determination, by successive approximations, of the values $P_0$, $P_1$, $q_1$, $P_2$, $q_2$, which, when inserted in the relation $$P(q) = P_0 + P_1 e^{-\frac{q}{q_1}} + P_2 e^{-\frac{q}{q_2}} \quad (A)$$

generate the curve which best approximates the experimental curve passing through all the points which represent the N values determined experimentally during the preceding stage a);

c) the archiving of the values $P_0$, $P_1$, $q_1$, $P_2$, $q_2$ found in this way.

DETAILED DESCRIPTION OF THE INVENTIONS

Figure 1:
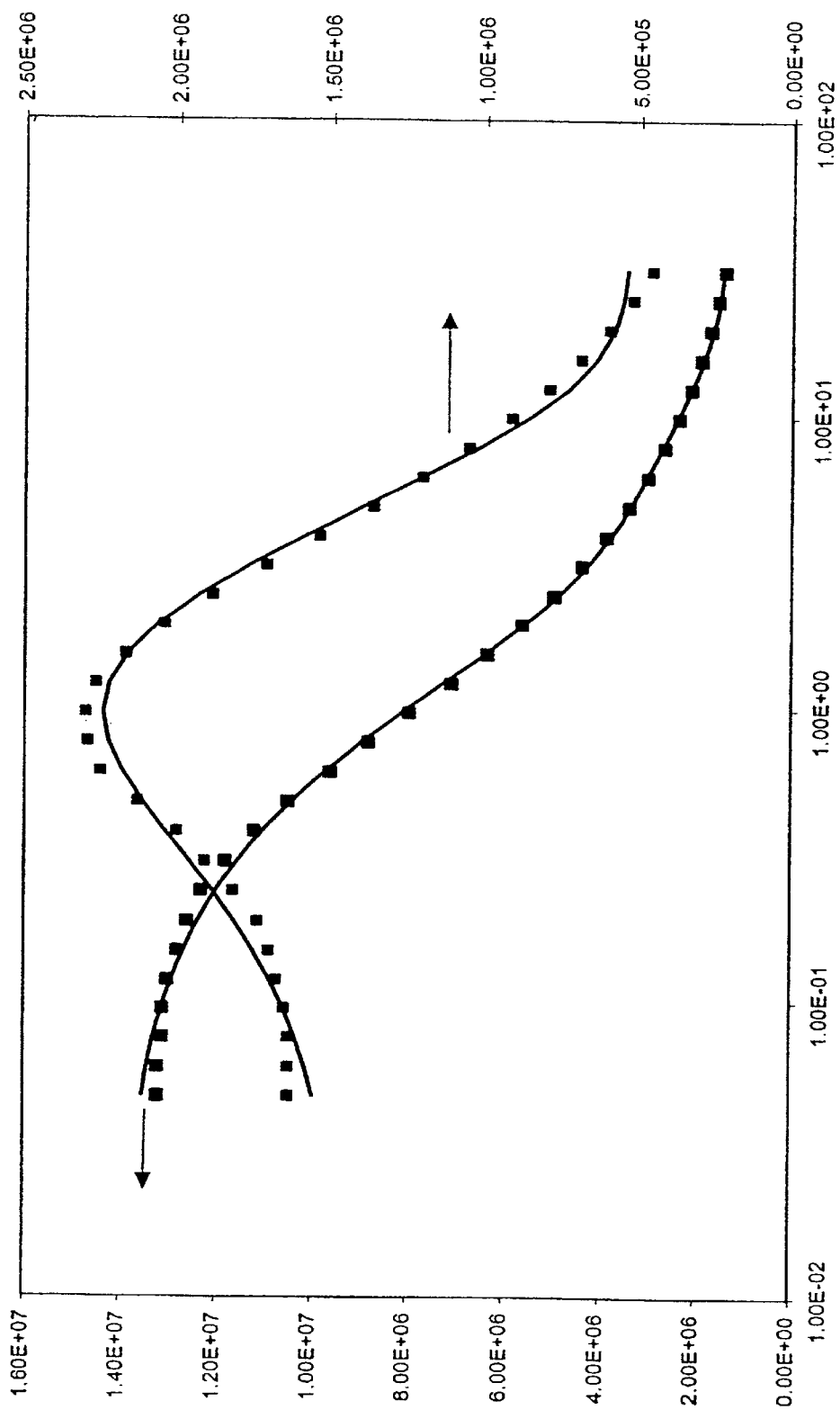
FIG. 1 illustrates a comparison between experimentally obtained data and calculated data according to the present invention.

The method according to the present invention can be used to improve the archiving of N measured experimental values of a dynamic parameter P where this parameter is a function of the deformation q at a given temperature, thus reducing the number of values to be archived from 2*N (for each acquisition the value of the measured dynamic parameter and the corresponding applied deformation must be archived) to 5. Since in order to characterize unambiguously the dynamic properties of a viscoelastic material it is necessary to know the behaviour of at least two dynamic parameters as a function of the deformation (for example, the modulus of elasticity and the viscous modulus), and since many measurements ($N \geq 5$) are generally required for each dynamic parameter, it is evident that the method according to the invention makes it possible to reduce significantly the number of values to be archived.

In a first embodiment, the said dynamic parameter P is the modulus of elasticity P' of the said viscoelastic material.

In a second embodiment, the said dynamic parameter P is the viscous modulus P" of the said viscoelastic material.

In a third embodiment, the said dynamic parameter P is the complex modulus P* of the said viscoelastic material.

In a fourth embodiment, the said dynamic parameter P is the loss factor $\tan\delta$ of the said viscoelastic material.

Additionally, after the acquisition of the N experimental measurements of the dynamic parameter of the viscoelastic material which are necessary to characterize the behaviour curve of the parameter under examination, stage b) comprises the stages of:

calculating P(q), for at least 5 values of deformation q read on the said experimental curve which passes through all the points which represent the N values determined experimentally in stage a), by means of the curve defined by the said relation (A) in which an arbitrary value is assigned to the 5 values $P_0, P_1, q_1, P_2, q_2$, calculating the differences between the values of P(q) calculated in this way and the corresponding values belonging to the said experimental curve, summing the squares of the aforesaid differences, minimizing the sum of the squares of the differences to obtain the values $P_0, P_1, q_1, P_2, q_2$ which, when inserted in the aforesaid relation (A), generate the curve which best approximates the said experimental curve.

Preferably, the values of deformation q used to calculate P(q) by means of the relation (A) are selected from those used in stage a). More preferably, they are all those used in stage a).

At this point, the 5 values $P_0, P_1, q_1, P_2, q_2$ obtained in this way can be archived, for example in a paper archive or in the memory of a computer, so that they can be used subsequently when required.

EXAMPLE 60 parts by weight of type N234 carbon black, together with the conventional vulcanizing agents, vulcanization accelerators, activators, anti-ageing substances and plasticizers well known in the production of tread mixes, were added to 100 parts by weight of a mix for tire treads consisting of a ternary mixture of 70 parts by weight of styrene butadiene rubber (SBR), 20 parts by weight of butadiene rubber (BR) and 10 parts by weight of natural rubber (NR). The mix produced in this way was then subjected to conventional sulphur-based vulcanization treatment at a temperature of 150° C. for 30 minutes. Finally, a cylindrical test specimen having a diameter of 10±0.2 mm and a height of 6±0.2 mm was prepared from this mix.

A torsion test was conducted on this test specimen at a frequency of 1 Hz and at a temperature of 23±2° C. for different values of the angle α of applied torsion, by means of a machine known as the Asphalt Analyzer made by the Rheometric company, previously prepared for analysing the behaviour of the test specimen over a range of deformations from 0.05% to 40%, with logarithmic scanning of the applied deformations.

With this arrangement, since the dependence of the deformation γ on the angle α of applied torsion is expressed by the following relation:

$$\gamma(\%) = \alpha \times R/h \times 100$$

where

R and h are the radius and height respectively of the cylindrical test specimen, the machine provided 29 pairs of measured values (deformation/value of parameter) for each of two parameters, namely the modulus of elasticity G' and the viscous modulus G", expressed in pascals (Pa).

Table 1 shows the 29 sets of three values found in this way.

TABLE 1

| γ% | G'(Pa) | G"(Pa) |
|---|---|---|
| 4.77E−02 | 1.32E+07 | 1.64E+06 |
| 5.97E−02 | 1.32E+07 | 1.64E+06 |
| 7.55E−02 | 1.31E+07 | 1.64E+06 |
| 9.50E−02 | 1.31E+07 | 1.65E+06 |
| 1.19E−01 | 1.30E+07 | 1.68E+06 |
| 1.50E−01 | 1.28E+07 | 1.70E+06 |
| 1.89E−01 | 1.26E+07 | 1.74E+06 |
| 2.39E−01 | 1.23E+07 | 1.82E+06 |
| 3.01E−01 | 1.18E+07 | 1.91E+06 |
| 3.81E−01 | 1.12E+07 | 2.00E+06 |
| 4.80E−01 | 1.05E+07 | 2.13E+06 |
| 6.06E−01 | 9.62E+06 | 2.25E+06 |
| 7.66E−01 | 8.82E+06 | 2.29E+06 |
| 9.67E−01 | 7.96E+06 | 2.30E+06 |
| 1.22E+00 | 7.08E+06 | 2.27E+06 |
| 1.54E+00 | 6.34E+06 | 2.17E+06 |
| 1.95E+00 | 5.63E+06 | 2.04E+06 |
| 2.46E+00 | 4.97E+06 | 1.89E+06 |
| 3.11E+00 | 4.40E+06 | 1.71E+06 |
| 3.92E+00 | 3.89E+06 | 1.54E+06 |
| 4.94E+00 | 3.42E+06 | 1.36E+06 |
| 6.23E+00 | 3.02E+06 | 1.20E+06 |
| 7.86E+00 | 2.67E+06 | 1.05E+06 |
| 9.91E+00 | 2.37E+06 | 9.15E+05 |
| 1.25E+01 | 2.11E+06 | 7.93E+05 |
| 1.57E+01 | 1.90E+06 | 6.92E+05 |
| 1.98E+01 | 1.71E+06 | 6.00E+05 |
| 2.50E+01 | 1.55E+06 | 5.24E+05 |
| 3.15E+01 | 1.41E+06 | 4.61E+05 |

By applying the method according to the invention as indicated above, the following values were obtained:

1. For G':

minimum sum of squares of the errors: $2.36 * 10^{10}$;

mean error: $1.54 * 10^5$, corresponding to the following values:

⇒$G'_0 = 1.39 * 10^6$;
⇒$G'_1 = 8.84 * 10^6$;
⇒$\gamma'_1 = 1.03$;
⇒$G'_2 = 3.72 * 10^6$;
⇒$\gamma'_2 = 7.66$.

2. For G":

minimum sum of squares of the errors: $2.93 * 10^9$;

mean error: $5.41 * 10^4$, corresponding to the following values:

⇒$G''_0 = 5.39 * 10^5$;
⇒$G''_1 = -1.36 * 10^6$;
⇒$\gamma''_1 = 0.467$;
⇒$G''_2 = 2.27 * 10^6$;
⇒$\gamma'_2 = 5.08$.

The number of values in Table 1 is 87, and this is true of the majority of cases. By using the method according to the invention, the values to be archived can be reduced from 87 to 10 (in the case of two dynamic parameters) and from 58 to 5 (in the case of one dynamic parameter). In other words, they can be reduced to approximately 11.5% or 8.6% of the initial number.

Clearly, therefore, the method according to the invention effectively resolves the problem tackled by the inventors.

FIG. 1 shows the comparison between the experimental curves of G' and G" respectively (in which the individual actual measurements are represented by small squares) and the curves plotted by the method according to the invention (continuous lines).

It can be seen that:

The mean error of the modulus of elasticity calculated by the method according to the invention is 2% of the measured mean value, while the maximum error of the calculated value is 2.5% of the corresponding measured value. In other words, the curve plotted by the method according to the invention shows a mean deviation of 2% from the curve obtained from the experimental values, and a maximum deviation of 2.5%.

Similarly, the mean error of the calculated viscous modulus is 3.5% of the measured mean value, and the maximum error of the calculated value is 5% of the corresponding measured value. In this case, therefore, the curve plotted by the method according to the invention shows a mean deviation of 3.5% from the curve obtained from the experimental values, and a maximum deviation of 5%.

Clearly, the method according to the invention accurately reproduces the experimental values, and the minimum deviations which are found do not detract in any way from the reliability of the subsequent calculations carried out on the basis of the calculated values of P', P", P* and tanδ as a function of q in the design of products such as tyres for motor vehicles.

What is claimed is:

1. A method for archiving a curve plotted from at least N (N≧5) experimentally measured values of a dynamic parameter P of a viscoelastic material, the dynamic parameter being a function of deformation q at a given temperature, said method comprising:

acquiring N experimental measurements of the dynamic parameter P of the viscoelastic material at a predetermined temperature;

determining, by successive approximations, values for $P_0$, $P_1$, $q_1$, $P_2$, and $q_2$, which, when inserted in the relation $$P(q) = P_0 + P_1 e^{\frac{-q}{q_1}} + P_2 e^{\frac{-q}{q_2}}$$

generate a curve that approximates an experimentally obtained curve passing through all the at least N experimentally measured values; and archiving the values $P_0$, $P_1$, $q_1$, $P_2$, and $q_2$.

2. The method of claim 1, wherein the dynamic parameter P is a modulus of elasticity P' of the viscoelastic material.

3. The method of claim 1, wherein the dynamic parameter P is a viscous modulus P" of the viscoelastic material.

4. The method of claim 1, wherein the dynamic parameter P is a complex modulus P* of the viscoelastic material.

5. The method of claim 1, wherein the dynamic parameter P is a loss factor tanδ of the viscoelastic material.

6. The method of any of the preceding claims 1 to 5, wherein the step of determining comprises:

calculating predicted values P(q), for at least five values of deformation q, according to a curve represented by $$P(q) = P_0 + P_1 e^{\frac{-q}{q_1}} + P_2 e^{\frac{-q}{q_2}}$$

in which arbitrary values are assigned to $P_0$, $P_1$, $q_1$, $P_2$, and $q_2$;

calculating differences between the predicted values of P(q) and corresponding experimentally measured values belonging to the experimentally obtained curve, summing squares of the differences, minimizing sums of the squares of the differences to obtain values for $P_0$, $P_1$, $q_1$, $P_2$, and $q_2$ which, when inserted into $$P(q) = P_0 + P_1 e^{\frac{-q}{q_1}} + P_2 e^{\frac{-q}{q_2}}$$

generate a curve which approximates the experimentally obtained curve.

7. The method of claim 6, wherein the at least five values of deformation q used to calculate P(q) using $$P(q) = P_0 + P_1 e^{\frac{-q}{q_1}} + P_2 e^{\frac{-q}{q_2}}$$

are selected from the values of q used in the acquiring step.

8. The method of claim 7, wherein the at least five values of deformation q used to calculate P(q) using $$P(q) = P_0 + P_1 e^{\frac{-q}{q_1}} + P_2 e^{\frac{-q}{q_2}}$$

a are all of the values of q used in the acquiring step.

* * * * *

UNITED STATES PATENT AND TRADEMARK OFFICE
CERTIFICATE OF CORRECTION

PATENT NO. : 6,341,531 B1
DATED : January 29, 2002
INVENTOR(S) : Antonio Brunacci et al.

It is certified that error appears in the above-identified patent and that said Letters Patent is hereby corrected as shown below:

Column 5,
Line 41, after "comprising", insert -- the steps of --.

Column 6,
Line 4, after "$q_2$", insert -- ; wherein $P_0$ represents a value of the dynamic parameter P at infinite deformation, $P_1$ represents a value of the dynamic parameter P at a first deformation, $q_1$ represents a characteristic deformation at which a first exponential intervenes, $P_2$ represents a value of the dynamic parameter P at a second deformation, and $q_2$ represents a characteristic deformation at which a second exponential intervenes --.

Column 6,
Lines 5, 7, 9 and 11, "wherein the" should read -- said --.
Line 13, "of any of" should read -- of any one of --.
Line 50, before "are", delete "a".

Signed and Sealed this

Eleventh Day of May, 2004

JON W. DUDAS
*Acting Director of the United States Patent and Trademark Office*